US00PP36958P2

(12) United States Plant Patent
Reynbery et al.

(10) Patent No.: US PP36,958 P2
(45) Date of Patent: Sep. 16, 2025

(54) ***CANNABIS* PLANT NAMED 'PTC8510V'**

(50) Latin Name: *Cannabis sativa*
Varietal Denomination: PTC8510V

(71) Applicant: Phylos Bioscience, Inc., Portland, OR (US)

(72) Inventors: Jared Reynbery, Portland, OR (US); Erica Bakker, Portland, OR (US)

(73) Assignee: Phylos Bioscience, Inc., Portland, OR (US)

( * ) Notice: Subject to any disclaimer, the term of this patent is extended or adjusted under 35 U.S.C. 154(b) by 0 days.

(21) Appl. No.: 18/902,526

(22) Filed: Sep. 30, 2024

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258, 263.1
CPC ... A01H 5/02; A01H 5/12; A01H 5/00; A01H 6/28
See application file for complete search history.

*Primary Examiner* — June Hwu
(74) *Attorney, Agent, or Firm* — Klarquist Sparkman, LLP

(57) ABSTRACT

A new *Cannabis* variety distinguished by its maturity time, apical dominance, internode length. flower trichome density, aroma. very high THCV:THC ratio, and total cannabinoid content.

2 Drawing Sheets

Latin name of the genus and species of the plant claimed: *Cannabis sativa.*

Variety denomination: 'PTC8510V'.

BACKGROUND

*Cannabis* is an annual, dioecious, flowering herb. *Cannabis* plants produce a variety of secondary metabolites, including cannabinoids, terpenoids, and other compounds, which are often secreted by glandular trichomes that occur most abundantly on the floral calyxes and bracts of female plants. Cannabinoids are the most studied group of secondary metabolites in *Cannabis*. Most exist in two forms, as acids and in neutral (decarboxylated) forms. The acid form is designated by an "A" at the end of its acronym (i.e. THCA). The biologically active forms for human consumption are the neutral forms. Cannabinoids are typically synthesized in the plant as acid forms. Although some decarboxylation can occur in the plant, it can be significantly increased post-harvest by thorough drying of plant material followed by heating it, often by either combustion, vaporization, or heating in an oven. For most cannabinoid producing purposes, only female plants are desired. The presence of male flowers is considered undesirable as pollination is known to reduce cannabinoid yield. For this reason, many *Cannabis* varieties are grown "sinsemilla" through vegetative (i.e., asexual) propagation.

SUMMARY

The present application relates to a new and distinct variety of *Cannabis* plant named 'PTC8510V'. This new *Cannabis* variety was selected when growing in a cultivated area in Hillsboro, Oregon. 'PTC8510V' is commercially known as "Powerhouse," and is also known by its breeder name 22TP1C-141-105.

'PTC8510V' is a selection resulting from pollen receiver plant ('21TP1B-3-7', unpatented), which has a THCV content of 14.17% and a THC content of 4.41%, crossed with pollen donor plant ('22TX1-2-59', unpatented), which has a THCV content of 10.55% and THC content of 15.65%. 112 seeds of this cross were planted Nov. 7, 2022. 'PTC8510V' was discovered and selected as a single plant from F1 seed and was subsequently clonally propagated.

Parent cultivar '21TP1B-3-7' is an early maturing (7-9 weeks) cultivar with low apical dominance, short internode lengths, flowers with moderate trichome density, a THCV content of 10-15%, and a THC content of 4-6%, resulting in a THCV:THC ratio of roughly 3:1. Parent cultivar '22TX1-2-59' is a medium maturing variety (8-9 weeks) with high apical dominance, long internode lengths, flowers with low trichome density, a THCV content of 10-13%, and a THC content of 13-16%, resulting in a THCV:THC ratio of roughly 1:1. For comparison, 'PTC8510V' is a medium maturing variety (8-10 weeks) with moderately low apical dominance, long internode length, flowers with moderate trichome density, a THCV content of 14-19%, and a THC content of 2-4%, resulting in a THCV:THC ratio of roughly 5:1.

'PTC8505V' is a cultivar that has been commercially available and is of similar pedigree to 'PTC8510V', but is not a direct parent or sibling. 'PTC8510V' is distinguished from 'PTC8505V' at least on the basis that 'PTC8510V' has a very high THCV:THC ratio of 5:1, a total THCV of 14.29-16.54%, and a spicy-lime like aroma. In contrast, 'PTC8505V' has at most a 3:1 ratio of THCV:THC, a total THCV of about 13.44%, and a piney, grassy aroma.

'PTC8510V' can be distinguished from other know *Cannabis* varieties at least by the following unique combination of characteristics: spicy lime-like aroma with hints of cedar, very high THCV:THC ratio (5:1), total THCV of 14.29-16.54%, total cannabinoid content of about 20%, medium maturity time, moderately low apical dominance, long internode length, and moderate flower trichome density.

'PTC8510V' was asexually reproduced for at least three cycles by apical and sub-apical semi-herbaceous stem cuttings in Hillsboro, Oregon. Asexual reproduction of 'PTC8510V' shows that the characteristics as herein described come true to form, are firmly fixed, and are established and transmitted through succeeding propagations.

BRIEF DESCRIPTION OF THE DRAWING(S)

Figure 1:
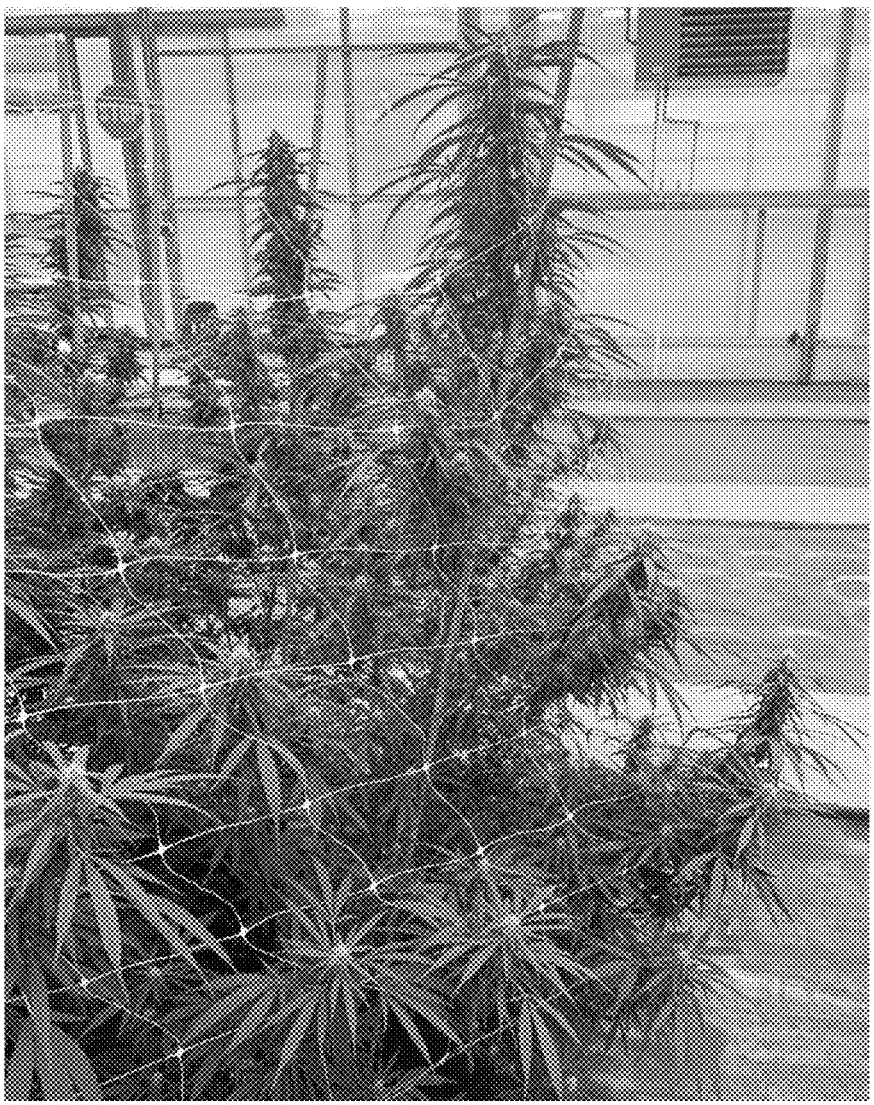
FIG. 1 shows an 86-day old greenhouse grown plant of 'PTC8510V'. The photograph was taken under ambient greenhouse light conditions in September 2024.
Figure 2:
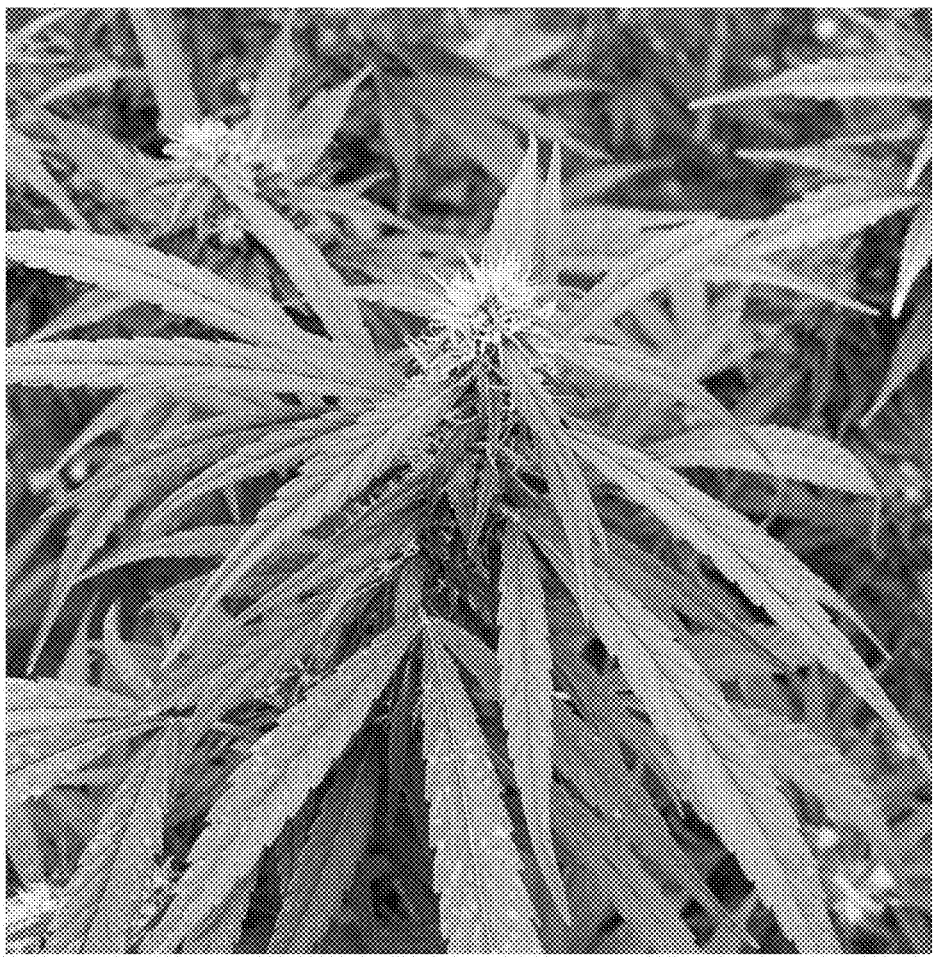
FIG. 2 shows a close-up of the flowers of 'PTC8510V'. The photograph was taken under ambient greenhouse light conditions in September 2024.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

The following detailed description of the 'PTC8510V' variety is based on observations of asexually reproduced progeny. Measurements were taken 35 days after flower initiation, unless otherwise indicated. The following detailed description concerns plants growing in a greenhouse in Hillsboro, Oregon. All color codes are hexadecimal color codes. Colors were detected using the Color Detector Android® smart phone application by Sadens Studio™ under ambient greenhouse light conditions in Hillsboro, Oregon.

Certain characteristics of this variety may change with changing environmental conditions (such as photoperiod, temperature, moisture, soil conditions, nutrient availability, or other factors) without change to the genotype. Color descriptions and other terminology are used in accordance with their ordinary dictionary descriptions, unless the context clearly indicates otherwise.

Scientific name: *Cannabis sativa.*

Parentage:

*Pollen receiver plant.*—'21TP1B-3-7'.

*Pollen plant.*—'22TX1-2-59'.

Plant:

*Growth habit.*—An upright, tap-rooted annual plant, forming fibrous roots when asexually propagated.

*Shape.*—Simple Erect.

*Plant height.*—1.53-1.74 m.

*Plant width.*—1-1.1 m.

*Flowering plant height.*—23-31 cm.

*Harvest plant height.*—85-101 cm.

*Plant stretch.*—54-76 cm.

*Plant % stretch.*—174-309.

*Plant wet biomass.*—0.51-0.72 kg.

*Plant wet bucked weight.*—0.38-0.61 kg.

*Proportion female plants.*—100% Pistillate.

*Proportion male plants.*—No staminate flowers produced naturally; however, can be induced with stress or ethylene-blocking compounds.

*Proportion hermaphrodite plants.*—Less than 5%.

*Time to harvest.*—10-12 weeks.

*Hardiness.*—Hardy to tolerant of warm and dry conditions without showing stress. Not tolerant to soil oversaturated with water for long periods. This plant has not been tested in outdoor conditions and therefore the USDA hardiness zone is unknown.

Stem:

*Stem shape.*—Hollow, ribbed, texture.

*Stem length.*—121-130 cm.

*Stem strength.*—Strong and upright.

*Stem diameter at base.*—2-2.1 cm.

*Stem color.*—C9E782.

*Stem texture.*—Smooth with shallow grooves.

*Depth of main stem ribs/grooves.*—Shallow.

*Internode length.*—3.2-8.4 cm.

Leaf:

*Shape.*—Palmately compound.

*Structure.*—Serrated margins, lightly acicular to lanceolate leaflets, tapering to an acuminate apex.

*Length at maturity (including petiole).*—17-21 cm.

*Average width.*—10.5 cm.

*Arrangement.*—Alternate.

*Margins.*—Jaggedly serrate with each tooth apex angled toward leaflet apex.

*Leaf color (adaxial).*—578C67.

*Leaf color (abaxial).*—70926A.

*Glossiness.*—Slightly glossy on the upper surface.

*Leaf hairs.*—Present on both upper and lower surfaces, predominant leaf hairs are glandular capitate-stalked.

*Petiole color.*—d9f577.

*Petiole anthocyanin color and intensity.*—E5D4BA; medium intensity during vegetative stage; strong during flowering stage.

*Petiole length.*—5.2-6.9 cm.

*Petiole diameter.*—1-2 mm.

*Petiole trichome type.*—Predominantly non-glandular.

*Stipule length at maturity.*—6-7 mm.

*Stipule width at maturity.*—<1 mm.

*Stipule shape.*—Linear with slight curvaceous growth.

*Stipule color.*—F0F3B5.

*Stipule trichome type.*—Predominantly glandular capitate-stalked.

*Number of leaflets.*—3-7.

*Central leaflet length.*—13-14 cm.

*Central leaflet width.*—2.6-3.2 cm.

*Central leaflet length/width ratio.*—4-4.8.

*Central leaflet number of teeth.*—22-24.

*Vein/midrib shape.*—Obliquely continuous throughout leaflet.

*Vein/midrib color.*—749855.

*Typical venation pattern.*—Pinnately veined leaflets.

*Sugar leaf.*—Palmately compound, 39 mm long and 32 mm wide. Predominant trichomes are glandular capitate-stalked. Upper-side sugar leaf color is 578C67 and lower-side leaf color is 70926A.

*Aroma.*—Spicy lime-like aroma with hints of cedar.

Female/pistillate flower:

*Inflorescence type.*—Elongated compound cymes.

*Inflorescence position.*—Terminal and axillary.

*Number of inflorescences per plant.*—110-170.

*Length of inflorescences.*—2-23 cm.

*Flower arrangement.*—Cymose.

*Flower shape.*—Urceolate.

*Flower (individual pistillate) length.*—4-6 mm.

*Flower (individual pistillate) depth.*—2-4 mm.
*Flower (compound cyme) diameter.*—5-5.5 cm.
*Petal description.*—Apetalous.
*Bract shape.*—Urceolate.
*Bract color.*—Upper surfaces and lower surfaces are 8FBF63.
*Typical bract number.*—3-200 bracts per inflorescence.
*Bract length.*—4-7 mm.
*Bract width.*—2-3 mm.
*Bract apex and base.*—Bracts have a rounded base and caudate apex.
*Bract texture.*—Smooth and covered with sticky trichomes.
*Bracteoles.*—Not present.
*Calyx shape.*—No defined calyx.
*Corolla.*—No defined corolla.
*Pistils per flower.*—One.
*Pistil length.*—8-10 mm.
*Stigma shape.*—Acute.
*Number of stigmas per flower.*—Two.
*Stigma length.*—3-8 mm.
*Stigma width.*—<1 mm.
*Stigma color.*—E8EDB0.
*Style.*—Average length is 5 mm, EB6734 in color at maturity.
*Trichome shape.*—Capitate-Stalked Glandular.
*Trichome color.*—A4B897.
*Terminal inflorescence shape.*—Oblong.
*Terminal inflorescence color.*—2D5416 & EBEEB4.
*Terminal inflorescence length.*—18-22 cm.
*Terminal inflorescence width.*—4-5.5 cm.
*Pedicel.*—Absent.
*Peduncle length.*—5 mm.
*Peduncle diameter.*—2 mm.
*Peduncle texture.*—Lightly ribbed.
*Peduncle color.*—559E57.
*Peduncle trichome.*—Predominantly non-glandular.
*Staminate shape.*—No staminate flowers produced naturally; however, male flower (staminate) can be induced with stress or ethylene-blocking compounds.
*Numbers of flowers per plant.*—Hundreds to thousands flowers per plant, multitudinous, congested with high concentrations on bushier wide inflorescence.
*Natural blooming time.*—Autumn.
*Fresh flower fragrance.*—Citrus/Pine.

Seed:

*Seed shape.*—Striped, smooth and globular.
*Seed size.*—1.6-2.3 mm.

TABLE 4

Cannabinoid Content (% dry weight of flower) as determined by High Performance Liquid Chromatography (HPLC).

| Metabolite | Minimum | Maximum |
|---|---|---|
| total CBD | 0 | 0 |
| total CBDV | 0.17 | 0.19 |
| total THC | 2.61 | 3.28 |
| total THCV | 14.29 | 16.54 |
| total cannabinoids | 17.07 | 19.58 |

TABLE 5

Terpene Content (% dry weight of flower) as determined by Gas Chromatography.

| Metabolite | Minimum | Maximum |
|---|---|---|
| alpha-pinene | 0.063 | 0.138 |
| camphene | 0.009 | 0.011 |
| beta-pinene | 0.073 | 0.124 |
| delta-3-carene | <LOQ | <LOQ |
| beta-myrcene | 0.572 | 1.739 |
| alpha-terpinene | <LOQ | <LOQ |
| D-limonene | 0.119 | 0.247 |
| beta-ocimene | 0.094 | 0.342 |
| p-cymene | <LOQ | <LOQ |
| gamma-terpinene | <LOQ | <LOQ |
| terpinolene | <LOQ | <LOQ |
| linalool | 0.044 | 0.076 |
| isopulegol | <LOQ | <LOQ |
| geraniol | <LOQ | <LOQ |
| beta-caryophyllene | 0.232 | 0.309 |
| alpha-humulene | 0.061 | 0.081 |
| nerolidol 1 | <LOQ | <LOQ |
| guaiol | 0.01 | 0.01 |
| caryophyllene oxide | <LOQ | <LOQ |
| alpha-bisabolol | 0.034 | 0.043 |
| eucalyptol | <LOQ | <LOQ |
| nerolidol 2 | 0.104 | 0.167 |
| total terpenes | 1.4 | 3.19 |

Top terpenes: Beta-myrcene, beta-ocimene, beta-caryophyllene, and D-limonene.

Disease/pest resistance: Unknown.

Molecular markers: A unique combination of 29 single nucleotide polymorphism (SNP) markers was identified for variety 'PTC8510V'. The markers are provided in Table 6. The combination of markers disclosed for 'PTC8510V' are unique to this variety, thus these markers can be used, for example, to genotype *Cannabis* plants to identify variety 'PTC8510V'.

TABLE 6

Single Nucleotide Polymorphism (SNP) Markers of 'PTC8510V'. The following table refers to chromosome positions of the publicly available Abacus Cannabis reference genome (Csat_AbacusV2, NCBI assembly accession GCA_025232715.1; also referred to as "CsaAba2").

| Chromosome | Position | SNP ID | REF | ALT | 'PTC8510V' |
|---|---|---|---|---|---|
| CsaAba2_1 | 37927202 | 141916_45118 | T | C | C/C |
| CsaAba2_1 | 42508653 | 262_823098 | G | T | G/G |
| CsaAba2_1 | 45592057 | 121785_197 | G | A | A/A |
| CsaAba2_2 | 4020302 | 167_3219271 | A | C | A/A |
| CsaAba2_2 | 6539925 | 167_940812 | T | C | C/C |
| CsaAba2_2 | 78649906 | 347_110280 | T | A | A/A |
| CsaAba2_2 | 91155632 | 158_767308 | G | A | G/G |
| CsaAba2_2 | 92450873 | 366_239268 | C | T | C/C |
| CsaAba2_3 | 14960943 | 120687_9128 | A | G | A/A |
| CsaAba2_3 | 53074525 | 141717_593569 | T | A | T/T |
| CsaAba2_3 | 76672303 | 142214_2388819 | C | G | G/G |
| CsaAba2_4 | 14480629 | 142704_8363492 | T | C | T/T |
| CsaAba2_4 | 33805380 | 142250_6863690 | G | A | G/G |
| CsaAba2_4 | 68786255 | 142078_499253 | C | A | C/C |
| CsaAba2_4 | 72692194 | 142078_3894722 | C | T | T/T |
| CsaAba2_4 | 73898859 | 142078_4996873 | T | C | T/T |
| CsaAba2_5 | 4965109 | 142050_513504 | C | T | C/C |

TABLE 6-continued

Single Nucleotide Polymorphism (SNP) Markers of 'PTC8510V'. The following table refers to chromosome positions of the publicly available Abacus Cannabis reference genome (Csat_AbacusV2, NCBI assembly accession GCA_025232715.1; also referred to as "CsaAba2").

| Chromosome | Position | SNP ID | REF | ALT | 'PTC8510V' |
|---|---|---|---|---|---|
| CsaAba2_5 | 75432249 | 422_2180389 | A | C | A/A |
| CsaAba2_6 | 74959100 | 164_2634629 | A | G | G/G |
| CsaAba2_8 | 9471523 | 171_8847435 | C | A | C/C |
| CsaAba2_8 | 52088446 | 141527_667545 | A | G | G/G |
| CsaAba2_9 | 9551328 | 424_4709922 | G | C | G/G |
| CsaAba2_9 | 10568626 | 424_5631426 | A | G | A/A |
| CsaAba2_X | 23172429 | 142055_4365541 | C | T | T/T |
| CsaAba2_X | 51310004 | 142293_5209347 | A | G | G/G |
| CsaAba2_X | 51844299 | 142293_5615610 | C | T | T/T |
| CsaAba2_X | 58645424 | 132592_6808 | G | T | T/T |

TABLE 6-continued

Single Nucleotide Polymorphism (SNP) Markers of 'PTC8510V'. The following table refers to chromosome positions of the publicly available Abacus Cannabis reference genome (Csat_AbacusV2, NCBI assembly accession GCA_025232715.1; also referred to as "CsaAba2").

| Chromosome | Position | SNP ID | REF | ALT | 'PTC8510V' |
|---|---|---|---|---|---|
| CsaAba2_X | 60242150 | 102945_11717 | T | C | C/C |
| CsaAba2_X | 71949822 | 421_5214874 | C | T | T/T |

We claim:

1. A new and distinct variety of *Cannabis* plant named 'PTC8510V', substantially as illustrated and described herein.

* * * * *